United States Patent
Gerstner et al.

(10) Patent No.: US 6,299,443 B1
(45) Date of Patent: Oct. 9, 2001

(54) DEVICE AND METHOD FOR CLEANING TEETH AND GUMS

(75) Inventors: Norbert Gerstner, Heidenheim; Michael Sauer, Bad Camberg; Norbert Schaefer, Frankfurt; Michael Stolper, Eschborn, all of (DE)

(73) Assignee: Braun GmbH, Frankfurt (DE)

( * ) Notice: Subject to any disclaimer, the term of this patent is extended or adjusted under 35 U.S.C. 154(b) by 0 days.

(21) Appl. No.: 09/395,312

(22) Filed: Sep. 13, 1999

Related U.S. Application Data

(63) Continuation of application No. PCT/EP98/08197, filed on Dec. 14, 1998.

(30) Foreign Application Priority Data

Jan. 16, 1998 (DE) .............................................. 198 01 362

(51) Int. Cl.[7] .............................. A61C 1/10; A61C 17/02
(52) U.S. Cl. ................................ 433/82; 433/80; 601/162
(58) Field of Search ................................... 433/82, 84, 80, 433/88; 601/162

(56) References Cited

U.S. PATENT DOCUMENTS

| | | | |
|---|---|---|---|
| 3,645,288 | * 2/1972 | Dawkins | 137/255 |
| 4,193,197 | * 3/1980 | Kuris et al. | 433/82 |
| 4,201,200 | 5/1980 | Hübner | 128/66 |
| 5,577,910 | * 11/1996 | Holland | 433/92 |

FOREIGN PATENT DOCUMENTS

| | | | |
|---|---|---|---|
| 27 35 427 A | 2/1979 | (DE) | A61C/17/02 |
| 35 45 868 A | 6/1987 | (DE) | A61C/17/02 |
| 1 310 303 A | 3/1973 | (GB) | B08B/3/02 |

\* cited by examiner

Primary Examiner—Nicholas D. Lucchesi
(74) Attorney, Agent, or Firm—Edward S. Podszus

(57) ABSTRACT

The invention is directed to a device (1) for cleaning teeth and gums, which is provided with a liquid container (2) that is joined by way of a liquid supply conduit (7) to an inlet (8) of a pump (9) adapted to be driven by an electric motor (10). The pump, when activated, draws a liquid (3) from the liquid container (2) to the inlet (8). Still further, an air supply conduit (13) is provided which is connected to the liquid supply conduit (7) for the purpose of admixing air to the drawn liquid (3). According to the invention, at least a section (15) of the air supply conduit (13) is arranged at a level above a maximum possible level (14) of the liquid (3). This prevents the escape of liquid (3) from the device (1).

23 Claims, 2 Drawing Sheets

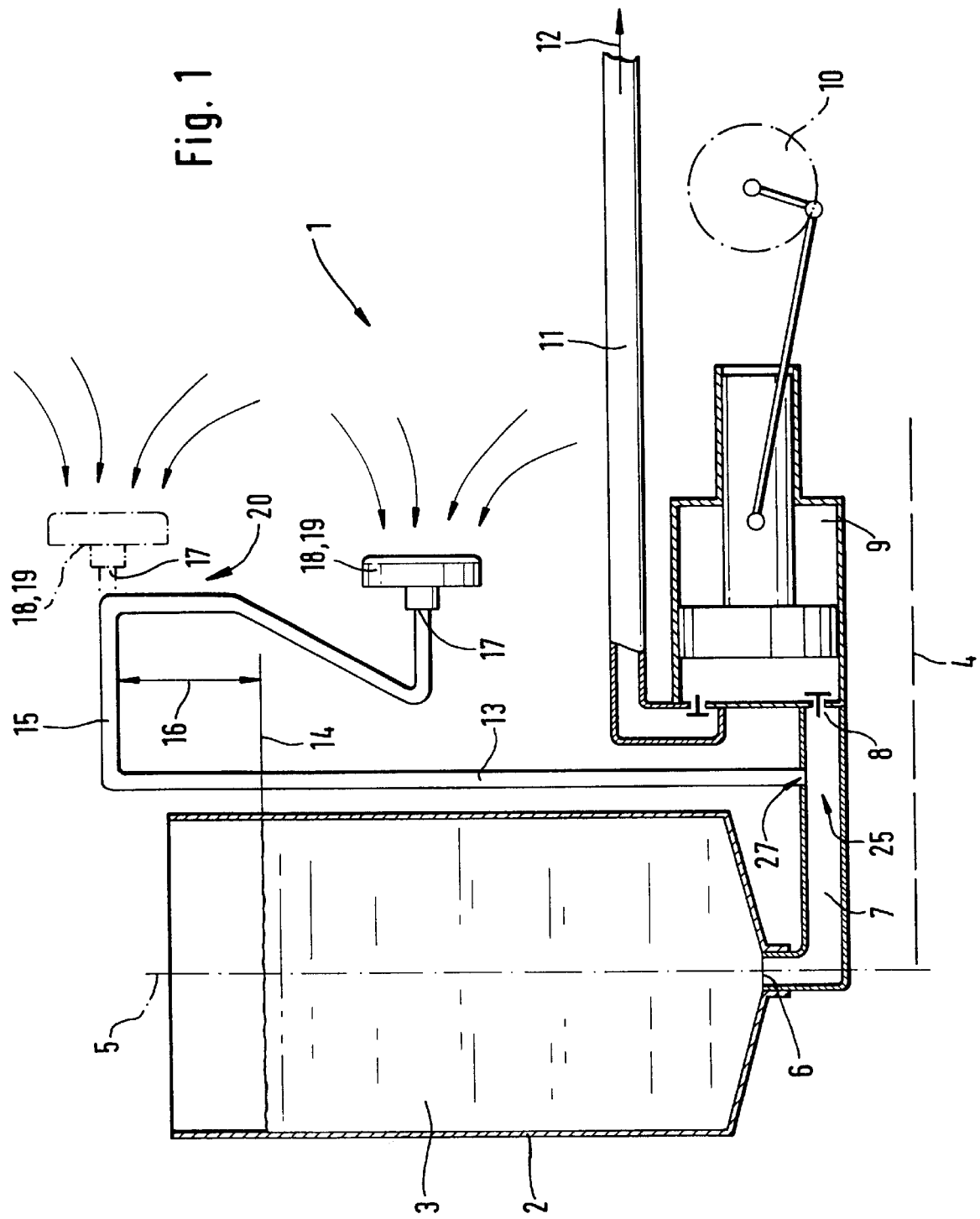

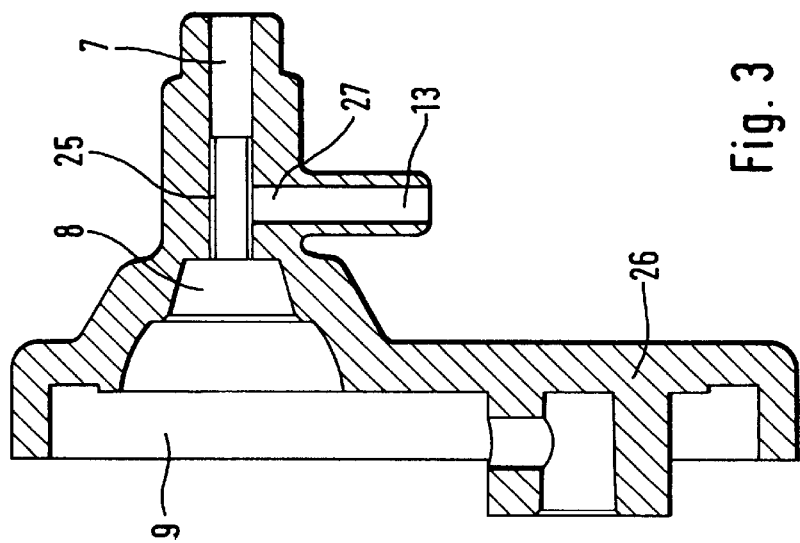
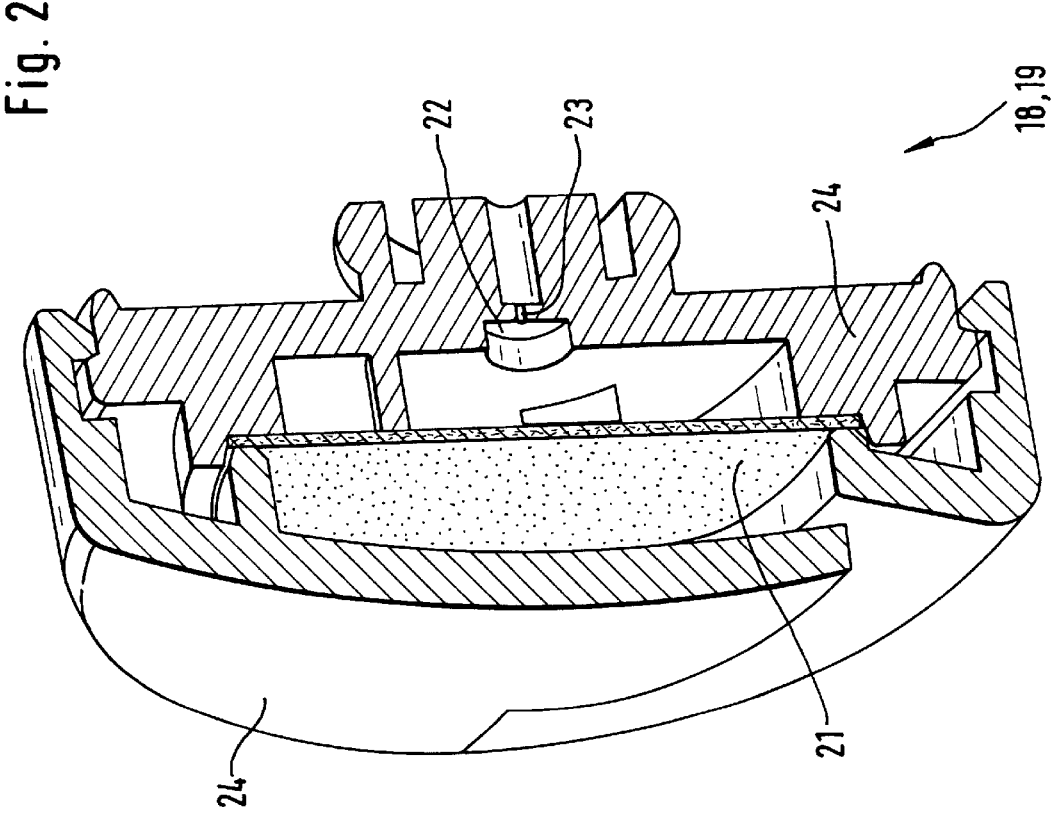

DEVICE AND METHOD FOR CLEANING TEETH AND GUMS

This is a continuation of International Application No. PCT/EP98/08197, pending, with an International filing date of Dec. 14, 1998.

This invention relates to a device for cleaning teeth and gums, with a liquid container that is joined by way of a liquid supply conduit to an inlet of a pump adapted to be driven by an electric motor, said pump, when activated, being adapted to draw a liquid from the liquid container to the inlet, and with an air supply conduit connected to the liquid supply conduit for the purpose of admixing air to the drawn liquid. Furthermore, the present invention relates to a method for cleaning teeth and gums, in which a liquid is adapted to be drawn from a liquid container through a liquid supply conduit to an inlet of a pump adapted to be driven by an electric motor, and in which air from, an air supply conduit joined to the liquid supply conduit is admixed to the drawn liquid.

A device of this type and a method of this type are known, from the German Offenlegungsschrift DE 27 35 427 A1.

This specification describes a device referred to as oral irrigator for cleaning teeth, in which a pump draws water from a container through a conduit and pumps it to a mouthpiece. Connected to the conduit is an air hose equipped with a valve which can be adjusted by a user. During operation of the oral irrigator, air from the air hose is admixed to the drawn water when the valve is set accordingly.

When the oral irrigator is deactivated the valve has to be closed by the user in order to prevent water escaping from the oral irrigator through the valve. This may result in operating errors by the user.

It is an object of the present invention to provide a device and a method for cleaning teeth and gums which enable the user to perform operations simply and reliably.

SUMMARY OF THE INVENTION

According to the present invention this object is accomplished with a device of the type initially referred to in that at least a section of the air supply conduit is arranged at a level above a maximum possible level of the liquid. Furthermore, according to the invention the object is accomplished with a method of the type initially referred to in that the supply of air in the air supply conduit proceeds at least partly at a level that is above a maximum possible level of the liquid.

Neither when the device of the present invention is activated nor deactivated is it possible, therefore, for liquid to escape from the air supply conduit. The highest the liquid in the air supply conduit can rise is to the said maximum possible level, which according to the invention is positioned below the said section of the air supply conduit. This section represents in particular the highest point of the air supply conduit and is, as previously mentioned, positioned at a level above the maximum possible level of the liquid inside the device.

Consequently, the user no longer needs to watch out that no liquid emerges from the device. This is prevented automatically by the invention.

As a further result of the invention there is also no need of a separate valve or the like. Arranging the section of air supply conduit above the maximum possible level of the liquid is itself enough, without additional components, to reliably prevent the emergence of any liquid.

Elimination of the valve also means that the costs and effort for manufacturing the device of the present invention are also reduced.

In advantageous embodiments of the invention a bend in the air supply conduit, particularly one of approximately U-shape, is positioned at a level above the maximum possible level of the liquid, and/or the free end of the air supply conduit is positioned above the maximum possible level of the liquid.

In both embodiments it is guaranteed that no liquid can escape from the air supply conduit. A further advantage of the first mentioned embodiment is that, thanks to the U-shaped bend, the air supply conduit can be returned to an area of the device of the present invention where sufficient space is available to accommodate further components needing to be connected to the air supply conduit.

In a further advantageous embodiment of the present invention, the air supply conduit has a filter to clean the air. This filter is arranged preferably at the free end of the air supply conduit. This ensures that all the air drawn into the air supply conduit is cleaned by the filter as it enters the conduit. Soiling of the device of the present invention is thus reliably prevented. Furthermore, considering that the air supply conduit proceeds from the filter at a level above the maximum possible liquid level as disclosed in the invention, it is guaranteed to be impossible for any liquid to reach and soil the filter.

In yet another advantageous embodiment of the present invention, the air supply conduit has a throttle in particular to control the amount of air supplied by way of the air supply conduit. This throttle is arranged preferably at the free end of the air supply conduit. It is thus possible to accommodate the filter and the throttle in a common housing. With a view to the structural design of the device of the present invention this represents a further simplification and hence a further possible cost reduction. Furthermore, considering that the air supply conduit proceeds from the throttle at a level above the maximum possible liquid level as disclosed in the invention, it is guaranteed to be impossible for any liquid to reach and soil the throttle and in particular for it to block its throughhole.

It is particularly advantageous for the filter to be positioned upstream of the throttle in the direction of the supplied air. This ensures that only air which has been previously cleaned by the filter actually reaches the throttle. Soiling and hence blocking of the throttle is thus reliably prevented, particularly if the throttle has a small throughhole.

In an advantageous further aspect of the present invention, the liquid supply conduit has a constriction particularly in the area of the junction of the air supply conduit to the liquid supply conduit. By means of this constriction, air is aspirated through the air supply conduit to the liquid supply conduit and hence admixed to the liquid in simple manner. The constriction can be produced by a T-piece, for example, which affords particular economy of manufacture.

In a further advantageous feature of the present invention, the air supply conduit in the form of a hose is laid independently of the liquid container inside particularly a housing of the device. By using a hose, the air supply conduit can be laid particularly easily and flexibly in the interior of the device of the invention. Furthermore, the hose represents a particularly low-cost way of producing the air supply conduit.

All in all the present invention results in a device which has no moving parts for aspiration of the air. Consequently the device according to the invention displays greater reliability and longer life.

Further features, application possibilities and advantages of the present invention will become apparent from the subsequent description of embodiments of the invention illustrated in the Figures of the accompanying drawing. It will be understood that any single feature and any combination of single features described or represented by illustration form the subject-matter of the present invention, irrespective of their summary in the patent claims or their back reference, as well as irrespective of their wording and representation in the description and the drawing, respectively.

BRIEF DESCRIPTION OF THE DRAWINGS

FIG. 1 is a schematic view of an embodiment of a device of the present invention for cleaning teeth and gums;

FIG. 2 is a schematic perspective view, partly sectioned, of a filter with a throttle for use in the device of FIG. 1; and FIG. 3 is a schematic sectional view of a T-piece for use in the device of FIG. 1.

FIG. 1 shows a device 1 enabling a user to clean his teeth and gums by supply of a liquid. The device 1 is called an oral irrigator, the liquid used being water.

DETAILED DESCRIPTION OF PREFERRED EMBODIMENTS

The device 1 has a liquid container 2 which is filled with a liquid 3. The device 1 with the liquid container 2 is placed on a horizontal surface 4 or the like in such a way as to produce the vertical axis identified by reference numeral 5 in FIG. 1.

At its deepest point in vertical direction the liquid container 2 is equipped with an outlet 6 having a liquid supply conduit 7 connected thereto. The liquid container 2 is joined by this liquid supply conduit 7 to an inlet 8 of a pump 9.

When activated, the pump 9 is driven by an electric motor 10. This causes the liquid 3 to be drawn from the liquid container 2 to the inlet 8 of the pump 9. The drawn liquid 3 is then pumped by the pump 9 through a further conduit 11 in the direction of the arrow 12 to a mouthpiece or the like, with which the user can spray the liquid 3 onto his teeth and gums.

An air supply conduit 13 is connected to the liquid supply conduit 7 at a location between the outlet 6 of the liquid container 2 and the inlet 8 of the pump 9. The air supply conduit 13 can be laid in the form of a hose, for example, independently of the liquid container 2 inside a housing of the device 1.

Inside the liquid container 2 the liquid 3 is able to adopt a maximum level 14. This maximum possible level 14 results when the liquid container 2 is essentially filled to capacity with the liquid 3. This condition is shown in FIG. 1.

The air supply conduit 13 is arranged inside the device 1 in such a way that at least a section 15 of the air supply conduit 13 runs above the maximum possible level 14 of the liquid 3. This is shown in FIG. 1 in that the section 15 of the air supply conduit 13 is arranged a distance 16 above the maximum possible level 14 of the liquid 3.

A filter 18 with a throttle 19 is positioned at the free end 17 of the air supply conduit 13. FIG. 1 shows two possible alternatives for the arrangement of the filter 18 and the throttle 19. Suitably, only one of the two alternatives will be realized in the device 1.

With the first alternative the filter 18 with the throttle 19 is positioned at a level below the maximum possible level 14 of the liquid 3. In this case the section 15 of the air supply conduit 13 represents an approximately U-shaped bend 20, and the free end 17 of the air supply conduit 13 is positioned underneath the maximum possible level 14 of the liquid 3.

With the second alternative the filter 18 with the throttle 19 is positioned at a level above the maximum possible level 14 of the liquid 3. In this case the free end 17 of the air supply conduit 13 is positioned likewise above the maximum possible level 14 of the liquid 3.

FIG. 2 shows an embodiment of the filter 18 with the throttle 19.

The filter 18 has a membrane 21 made of PTFE. Alternatively the membrane 21 can also be made of paper, glass fibers or the like. The material of the filter 18 is selected so that ideally it will not need to be replaced within the life-span of the device 1.

The throttle 19 has a ruby 22 or the like equipped with a through-hole 23. The diameter of the through-hole 23 is small, measuring around 100 $\mu$m, for example.

The throttle 19 is positioned between the filter 18 and the air supply conduit 13 and hence downstream of the filter 18 in the direction of the supplied air.

The filter 18 and the throttle 19 are accommodated in a common housing 24. It is also possible, however, for the filter 18 and the throttle 19 to be constructed independently of each other and for them to be positioned at different locations in the air supply conduit 13.

A constriction 25 is provided in the liquid supply conduit 7, particularly in the area of the junction with the air supply conduit 13.

FIG. 3 shows an embodiment of the constriction 25.

The inlet 8 of the pump 9, a section of the liquid supply conduit 7 and a section of the air supply conduit 13 are integrated in a casing 26 of the pump 9 where they form a so-called T-piece 27. The constriction 25 in the liquid supply conduit 7 is positioned in the area of the T-piece 27.

When activated, the pump 9 draws liquid 3 from the liquid container 2 through the liquid supply conduit 7. A pressure below atmospheric develops in the air supply conduit 13 as the result, inter alia, of the constriction 25 in the liquid supply conduit 7. This results in air being aspirated through the filter 18, the throttle 19 and the section 15 of the air supply conduit 13 to the liquid supply conduit 7. In the T-piece 27 the aspirated air mixes with the drawn liquid 3.

The constriction 25 is intended in particular to produce the pressure below atmospheric in the air supply conduit 13 needed to aspirate the air. The throttle 19 is intended in particular to meter and control the volume of aspirated air by means of the through-hole 23. The constriction 25 and the throttle 19 are coordinated in such a way that, without the throttle 19, the constriction 25 would produce a volumetric flow greater than the volumetric flow possible through the throttle 19.

The filter 18 positioned upstream of the throttle 18 in the direction of the supplied air is used for cleaning the aspirated air. The filter 18 is designed in particular to have no throttling effect on the aspiration of the air.

Arranging at least section 15 of the air supply conduit 13 at a level above the maximum possible level 14 of the liquid 3 means that it is impossible for liquid 3 to escape from the device 1 through the air supply conduit 13. The air supply conduit 13 can be filled with the liquid no higher than to level 14, making it impossible for liquid 3 to reach the free end 17 of the air supply conduit 13.

This applies to both alternatives shown in FIG. 1, hence in particular also when the free end 17 of the air supply conduit 13 is positioned at a level below the maximum possible level 14 of the liquid 3, provided at least section 15 of the air supply conduit 13 is arranged above the level 14.

Furthermore, by arranging at least section 15 of the air supply conduit 13 above the maximum possible level 14 of the liquid 3, neither the filter 18 arranged at the free end 17 of the air supply conduit 13 nor the throttle 19 is exposed to the liquid 3. Since section 15 of the air supply conduit 13 is positioned above the maximum level 14 of the liquid 3, it is impossible for the liquid 3 to reach either the filter 18 or the throttle 19.

Should this occur due to an operating error by the user, the filter 18 and the throttle 19 will be emptied again automatically during normal operation of the device 1.

The liquid container 2 can be of detachable design. If the liquid container 2 is removed by the user, any liquid 3 contained in the air supply conduit 13 will empty into the liquid supply conduit 7 and the inlet 8 of the pump 9 and be received there and also, if necessary, inside the pump 9.

What is claimed is:

1. A device for cleaning teeth and gums, comprising
    a liquid reservoir defining a chamber having a maximum liquid fill level, the liquid reservoir being connected by a liquid supply conduit to an inlet of a pump adapted to be driven by an electric motor, said pump when activated being adapted to draw liquid from the liquid reservoir to the pump inlet, and
    an air supply conduit having an air inlet and an air outlet connected to the liquid supply conduit for admixing air to the drawn liquid, wherein at least a portion of the air supply conduit is disposed at a level above the maximum liquid fill level,
    whereby liquid from the reservoir is inhibited from escaping through the air supply conduit.

2. The device as claimed in claim 1, wherein an approximately U-shaped bend in the air supply conduit is positioned above the maximum liquid fill level.

3. The device as claimed in claim 1, wherein the air inlet of the air supply conduit is positioned above the maximum liquid fill level.

4. The device as claimed in claim 1, wherein the air supply conduit has a filter to filter the air.

5. The device as claimed in claim 4, wherein the filter is arranged at the air inlet of the air supply conduit.

6. The device as claimed in claim 4, wherein the filter has a membrane comprising PTFE.

7. The device as claimed in claim 4, wherein the filter has a membrane comprising a material chosen from the group consisting of paper and glass fiber.

8. The device as claimed in claim 4, wherein
    the air supply conduit further has a throttle for regulating the amount of air supplied through the air supply conduit, and
    the filter is positioned upstream of the throttle in the direction of the air inlet.

9. The device as claimed in claim 1, wherein the air supply conduit further has a throttle for regulating the amount of air supplied through the air supply conduit.

10. The device as claimed in claim 9, wherein the throttle is arranged at the air inlet of the air supply conduit.

11. The device as claimed in claim 9, wherein the throttle has a ruby or stone-like material provided with a small through-hole.

12. The device as claimed in claim 1, wherein the liquid supply conduit has a constriction in the area of the junction of the air supply conduit to the liquid supply conduit.

13. The device as claimed in claim 1, wherein the air supply conduit comprises a hose disposed independently of the liquid reservoir inside a housing containing the device.

14. The device as claimed in claim 1, wherein the liquid reservoir is detachably mounted to a housing containing the device, and that when the liquid reservoir is detached liquid contained in the air supply conduit is passed by the air outlet to the inlet of the pump.

15. The device as claimed in claim 1, wherein said maximum liquid fill level is defined in a direction of maximum admissible filling of the reservoir corresponding to a maximum height opposing a direction of gravitational force acting on liquid in the reservoir.

16. The device as claimed in claim 1, wherein the liquid supply conduit has a conduit inlet connected to an outlet orifice of the reservoir, and
    the air outlet is connected to the liquid supply conduit downstream of the conduit inlet.

17. The device as claimed in claim 1, wherein the air outlet is connected to the liquid supply conduit between the reservoir and the pump inlet.

18. The device as claimed in claim 1, wherein the air supply conduit outlet is connected to the liquid supply conduit proximate the pump inlet so that admixed air is drawn into the pump inlet with the drawn liquid.

19. The device as claimed in claim 1, wherein the portion of the air supply conduit that is disposed at a level above the maximum liquid fill level includes an extended portion of the air supply conduit located between said air inlet and said air outlet.

20. The device as claimed in claim 1, wherein the air inlet is free of a check valve completely occluding communication with an external surrounding air environment.

21. The device as claimed in claim 1, wherein the pump is disposed substantially below the reservoir.

22. A method for cleaning teeth and gums, comprising the steps of
    providing a liquid reservoir defining a chamber having a maximum liquid fill level, a liquid supply conduit connecting the liquid reservoir to an inlet of a pump adapted to be driven by an electric motor and having a pump outlet connected to a delivery mouthpiece, and an air supply conduit having an air inlet and an air outlet joined to the liquid supply conduit,
    drawing liquid from the reservoir through the liquid supply conduit to the pump inlet by driving the pump,
    supplying, while performing said step of drawing liquid, air moving from the air inlet into the air supply conduit through a region spatially above the maximum liquid fill level,
    admixing said supplied moving air from the air outlet into the liquid supply conduit, and
    discharging admixed liquid and air to the delivery mouthpiece, whereby reservoir liquid is inhibited from escaping through the air supply conduit.

23. The method as claimed in claim 22, wherein, in said step of providing, said maximum liquid fill level is defined in a direction of maximun admissible filling of the reservoir corresponding to a maximum height opposing a direction of gravitational force acting on liquid in the reservoir.

* * * * *